(12) United States Patent
Wassermann et al.

(10) Patent No.: US 12,331,284 B2
(45) Date of Patent: *Jun. 17, 2025

(54) COUPLED SORTING AND ELECTRIC TREATMENT OF BIOLOGICAL CELLS

(71) Applicant: AIT AUSTRIAN INSTITUTE OF TECHNOLOGY GMBH, Vienna (AT)

(72) Inventors: Klemens Wassermann, Korneuburg (AT); Terje Wimberger, Vienna (AT); Johannes Peham, Vienna (AT)

(73) Assignee: AIT AUSTRIAN INSTITUTE OF TECHNOLOGY GMBH, Vienna (AT)

( * ) Notice: Subject to any disclaimer, the term of this patent is extended or adjusted under 35 U.S.C. 154(b) by 1039 days.

This patent is subject to a terminal disclaimer.

(21) Appl. No.: 17/299,476

(22) PCT Filed: Dec. 12, 2019

(86) PCT No.: PCT/EP2019/084790
§ 371 (c)(1),
(2) Date: Jun. 3, 2021

(87) PCT Pub. No.: WO2020/120650
PCT Pub. Date: Jun. 18, 2020

(65) Prior Publication Data
US 2022/0049208 A1    Feb. 17, 2022

(30) Foreign Application Priority Data
Dec. 12, 2018 (EP) ..................... 18211954

(51) Int. Cl.
C12N 13/00 (2006.01)
C12M 1/00 (2006.01)
C12M 1/42 (2006.01)
C12Q 3/00 (2006.01)

(52) U.S. Cl.
CPC ............. *C12N 13/00* (2013.01); *C12M 35/02* (2013.01); *C12M 47/04* (2013.01); *C12M 47/06* (2013.01); *C12Q 3/00* (2013.01)

(58) Field of Classification Search
None
See application file for complete search history.

(56) References Cited

U.S. PATENT DOCUMENTS

| 10,391,187 B2 | 8/2019 | Ito et al. |
| 2010/0178682 A1* | 7/2010 | Nakada ................. C12M 47/04 435/173.9 |
| 2011/0189650 A1 | 8/2011 | Ayliffe et al. |

FOREIGN PATENT DOCUMENTS

| EP | 1797956 A1 | 6/2007 |
| WO | 00/63408 A2 | 10/2000 |
| WO | 2006/083907 A2 | 8/2006 |
| WO | 2009/100516 A1 | 8/2009 |
| WO | 2015/044191 A1 | 4/2015 |

OTHER PUBLICATIONS

European Search Report received for Application No. 18211954.5, dated Jun. 5, 2019.
International Search Report and Written Opinion received for PCT/EP2019/084790, mailed Mar. 23, 2020.
Schindelin, J., et al., "Fiji: an open-source platform for biological-image analysis," Nature Methods, Jul. 2012, vol. 9, No. 7, pp. 676-682.
Schut, T., et al., "A New Principle of Cell Sorting by Using Selective Electroporation in a Modified Flow Cytometer," Cytometry, 1990, vol. 11, pp. 659-666.
Wassermann, K., et al., "High-k Dielectric Passivation: Novel Considerations Enabling Cell Specific Lysis Induced by Electric Fields," ACS Applied Materials & Interfaces, 2016, 27 pages.
Office Action received for Chinese Application No. 201980082463.8, dated Feb. 1, 2024.

* cited by examiner

*Primary Examiner* — Michelle F. Paguio Frising
(74) *Attorney, Agent, or Firm* — Greer, Burns & Crain, Ltd

(57) ABSTRACT

The present application provides the following method for lysis or electroporation of cells in a biological sample:
  passing cells of the sample, suspended in a fluid, through a flow path with a preset flow speed, the flow path runs through a detection apparatus for detecting individual cells and the flow path includes at least two electrodes for generating an electric field, the electrodes are located downstream of the detection apparatus and are coated with a dielectric material with a relative permittivity greater than 3.9, wherein the coating at least covers the surface of the electrodes that faces the flow path, and
  when the presence of a specific cell is detected in the detection apparatus, then an electric field is generated between the electrodes when the detected cell passes between the electrodes in dependence of the flow speed, wherein the electric field causes electroporation or lysis of the cell.

31 Claims, 3 Drawing Sheets

COUPLED SORTING AND ELECTRIC TREATMENT OF BIOLOGICAL CELLS

BACKGROUND

The present invention relates to the fields of electroporation, lysis and sorting of cells.

Cell sorting is a method that allows to separate specific cells or cell populations from a biological sample with different cells. The basic principle that underlies many of the known methods is that in a first step the cells are guided through a narrow flow path with a detector which allows the identification of the cells based on their properties, e.g. by scattering of light, reflection, electrical loads or fluorescence. The properties which allow to distinguish the cells can be cell-inherent or artificially attached by means of cell-specific markers loading into or onto the cells. The cells of interest are identified and usually counted. This step is referred to a flow cytometry. Subsequent to identification, the identified cells are either counted or separated, e.g. by transferring them into separate repositories.

Other methods, such as Magnetic Activated Cell Sorting (MACS), require surface labelling of cells with magnetic beads prior to sorting. For example, in MACS the sample containing several cell types is mixed with magnetized markers that only attach to a certain cell type. In other words, a specific cell type is tagged. Then, the sample is transferred through a magnetic field, which separates the tagged cells from the untagged cells.

Today, the "Fluorescent Activated Cell Sorting" (FACS)-method is the most prominent and commercially relevant cell sorting method. According to this method, flow cytometry is used for fast identification of single cells based on their optical properties. Usually, cells of a sample are injected into a flow path of a flow cytometry apparatus and stimulated with a laser beam one after another. To this end, the cells are flushed through the flow path which has approximately the diameter of a single cell, so that each cell can be detected individually. The scattered light of each cell is then analysed and used for its identification. After identification, the cells are sorted. For this purpose, FACS uses electrical polarisation of the cells. Upon activation of an electric field, the polarized cells are deflected into the designated repositories, depending on the intensity of the electric field strength.

Another approach is shown in US 2011/0189650 A1, which combines flow cytometry with electroporation. The electroporation is within an interrogation zone that is associated with the detector, in particular, the interrogation zone is part of the detecting area in the flow path. The electric treatment of US 2011/0189650 A1 follows the Coulter principle: electrodes are placed upstream and downstream of an aperture. Once a cell passes the aperture, the impedance between the electrodes changes and can be measured. A detected cell can be electroporated. This system requires that a current flows between the electrodes between the electrodes and through the medium in which the cells are transported through the aperture—hence the electrodes can be placed in different legs of a turn (see e.g. FIG. 5 of US 2011/0189650 A1). To produce a current, the electrodes are uncoated. This system—although necessary—has the drawback that the currents lead to chemical reactions within the flow path that might negatively affect subsequent cells within the flow path. Furthermore, the required intensity of the required applied voltage is rather high due to the electrode setup.

A similar set-up is described in Schut et al. (Cytometry 11:659-666, 1990), especially FIG. 2A. Here again a pair of electrodes is placed upstream and downstream of an orifice. At the orifice, an optical detection system is placed similar to a standard flow cytometer. In chambers upstream and downstream of the orifice, electrodes are placed that allows to create a current in said chambers flowing through the orifice. This allows a separate counting of the cells via a Coulter counter. If higher voltages are applied to the same electrodes, then cells can be electroporated or lysed in the chambers but mostly in the orifice. The authors state that the temperature in the orifice can be high due to the electric currents there (p. 665). For lysis, this temperature increase is desired. Passage through the orifice limits the cells that can be treated by the electric current.

Various methods for lysis and electroporation of cells in biological samples are known. Lysis and electroporation can be specific for certain cells, thus obviating the need for any cell differentiation or cell sorting. E.g. WO 2015/044191 A1 describes selective lysis of non-pathogenic cells in a suspension of cells for further examination of pathogenic cells, such as bacteria, fungi or protozoa. This system requires tuning of electric parameters to selectively affect the cells.

It is an objective of the present invention to provide targeted electroporation or lysis of selected cells without affecting other cells. In an associated aspect, it is an objective of the present invention to provide an apparatus for specific lysis of cells in a biological sample that allows the targeted electroporation or lysis of selected cells without affecting other cells.

Summary

The present invention provides a method for lysis or electroporation of cells in a biological sample comprising the following steps:
  passing cells of the sample, preferably suspended in a fluid, through a flow path with a preset flow speed, wherein the flow path runs through a detection apparatus for detecting individual cells and wherein the flow path comprises at least two electrodes for generating an electric field, which electrodes are located downstream to the detection apparatus and which electrodes are coated with a dielectric material with a relative permittivity greater than 3.9, preferably greater than 9, more preferably 60 or more, wherein the coating at least covers the surface of the electrodes that faces the flow path, and
  when the presence of a specific cell is detected in the detection apparatus, then an electric field is generated between the electrodes when the detected cell passes between the electrodes in dependence of the flow speed, wherein the electric field causes electroporation or lysis of the cell.

The invention further provides an apparatus for specific lysis of cells in a biological sample with a flow path, preferably a capillary, that runs through a detection apparatus for detecting individual cells and with a pump unit that passes the cells through the flow path with a preset flow speed, wherein the flow path comprises at least two electrodes for generating an electric field, which electrodes are located downstream to the detection apparatus and which electrodes are coated with a dielectric material with a relative permittivity greater than 3.9, preferably greater than 9, more preferably 60 or more, wherein the coating at least covers the surface of the electrodes that faces the flow path.

All aspects relate to each other and any embodiment described for one aspect commensurately also relates to all other aspects and embodiments. E.g. the biological sample described for the method or the apparatus for the method can be included or can be part of the apparatus. The apparatus or any part thereof can be used in the inventive methods in all its embodiments and preferments.

Detailed Description

The invention provides an apparatus and a method for lysis or electroporation of cells in a biological sample comprising the following steps:
- passing cells of the sample, preferably suspended in a fluid, through a flow path with a flow speed, wherein the flow path runs through a detection apparatus for detecting individual cells and wherein the flow path comprises at least two electrodes for generating an electric field, which electrodes are located downstream to the detection apparatus and which electrodes are coated with a dielectric material with a relative permittivity greater than 3.9, preferably greater than 9, more preferably 60 or more, wherein the coating at least covers the surface of the electrodes that faces the flow path, and
- when the presence of a specific cell is detected in the detection apparatus, then an electric field is generated between the electrodes when the detected cell passes between the electrodes in dependence of the flow speed, wherein the electric field causes electroporation or lysis of the cell.

In the inventive apparatus and method, the electrodes are located downstream in the flow path so that the electric field does not affect the detection apparatus, which is upstream. Also, the electrodes are passivated with a coating with a relative permittivity greater than 3.9 (also referred to as high-k coating or material). This passivation prevents a faradaic current between the electrodes or at least reduces it so that substantially no faradaic current occurs, when the electric field is applied. This prevention of a current depends on the permittivity value of the coating. As shown herein, said passivation leads to improved treatment and reduced electrochemical side reactions. The inventive set-up also has the benefit that detection, which is usually performed according to a flow cytometry, i.e. the detector and the associated flow path are preferably a flow cytometer.

Cells are encased cellular bodies comprising a lipid membrane envelope, like liposomes, exosomes or microbubbles. Preferably the cells are biological cells with nucleus like leukocytes or disseminated cells, especially disseminated tumor cells, or without nucleus, like erythrocytes. Preferably the cell is a eukaryotic cell, or more generally comprises a cell membrane from an eukaryotic cell. Without being limited to a particular theory, it appears that the eukaryotic cell wall is specifically susceptible for manipulation by the inventive methods for electroporation or lysis, i.e. inducing leakiness or rupture of the cell membrane, respectively. In other embodiments it can also be a prokaryotic cell. Preferably the cell has no cell wall, which allows easier manipulation. In particular preferred are animal cells, especially of higher multicellular animals, even more preferred mammal, marsupial, avian, reptile, amphibian, insect or fish cells.

Surprisingly, it was found that biological cells, in particular eukaryotic cells, have particular discernible susceptibilities to the electric parameters in a chamber with coated electrodes according to the invention so that different cells can be individually targeted without affecting other cells. Thus it is also possible to make rough separation in the flow channel and groups of cells may pass the restricted flow channel at the detector. Still, individual cell passage is preferred. Cell specific electric treatment allows specific manipulation in a selected type of cells (subgroups of cells in the sample). In particular surprising was that the size of cells is not a relevant factor. In prior art, only the larger cells in a mixture could be targeted. According to the invention, also targeting the smaller cells in a sample of larger cells is possible, wherein the larger ones remain unaffected or less affected. Cells that can be distinguished (i.e. differently affected by said electric field) are for example tumor cells and non-tumor cells (each forming a different subgroup). With a suitable electric field parameter, also cells within these group can be distinguished, such as cells from different tissue origins, such as leukocytes, liver cells, kidney cells, erythrocytes, neuronal cells, fat cells, bone cells, cartilage cells, skin cells, epithelial cells, muscular cells etc. Also, the organism can be distinguished, such as animals, like vertebrate, and non-vertebrate or mammals, fish, amphibians, birds, reptiles, insects etc and bacteria. Preferably the cells of all subgroups are from an animal or human. Human cells are particularly preferred, e.g. preferably tumor cells from a human are distinguished from non-tumor cells from a human, e.g. but not necessarily the same human providing the tumor cells.

Inside the cell, there is usually an aqueous medium. Thus, with the outside also being an aqueous medium, the lipid envelope usually comprises a lipid bilayer. The lipid membrane is affected by the electric field, which can cause the formation of pores or holes (electroporation) or disruption of parts or the entire lipid membrane (lysis). Electroporation can be reversible electroporation. The specific nature of the electric parameters (strength, potential (voltage), pulse frequency, shape, duration, pulse amount or exerted energy on the cells by the electric field) not only depends on the cells of interest to be treated (either specifically or non-specifically). The absolute values also depend on the shape of the chamber—in particular the distance of the electrodes, the thickness of the dielectric material and the medium in which the cells are suspended. Different dielectric constants in the medium, different salt types etc. further affect the efficiency of the electric field so that the electric parameters need adjustment. However, it is possible to select a suitable set of parameters within the guidance provided herein without undue burden due to ease of adjusting electric properties and ease of testing cells. Effects of electroporation and lysis can be easily monitored by e.g. determining leakage of a marker that leaks out of or into the cells when the electric field is applied. The following description of parameters are preferred parameters within which cells can usually be distinguished due to their susceptibility to the electric field.

A specific cell is detected in the detector. This cell is also referred to as a cell of interest. The cell can be detected by physical or electrical or optical parameters, among others. Physical characteristics are e.g. its size or radioactivity (usually after labelling). An electrical parameter can be the cells impedance, which can be detected, e.g. by the Coulter principle. Optical characteristics include colour, especially fluorescence, light scattering, or reflectance, and transparency or opalescence. The identification can be facilitated by a detector that is tuned to receive one or more of these characteristics and transmit a signal. Any cellular characteristics can be used. Some characteristics may be reminiscent of a group of diverse cells. E.g. the inventive method can comprise selecting detection parameters to identify certain cells or populations (subgroups) of cells. Accordingly, the biological sample may comprise cells of a first (sub)group and cells of a second or more (sub)group(s), wherein cells of the first group are exposed to a first electric field with a first electric field strength and cells of the second group are exposed to a second electric field with a second electric field strength. One of the first or second group may be untreated with a first or second, respectively, electric field being absent or below an electroporation or lysis strength for the given cell type of the (sub)group.

Specific treatment of the cells, e.g. by selecting specific parameters of the electric field, can cause lysis of the cells of the first (sub)group and reversible electroporation of the cells of the second (sub)group.

The invention also provides an embodiment in which specific cells are collected after flowing through the chamber—having been specifically detected in the detector. The inventive apparatus may have a collection container for this purpose.

Some cells of interest may be labelled, such as by radioactive labels or fluorescent labels in order to cause detection. Such labelling can be contacting with a dye. Other labelling method include introducing a label inside the cell. The latter form of labelling can include a further electroporation step (distinct from the electroporation after the flow cell) wherein prior to passing the cells through the detection apparatus, electroporation for loading the cells with a marker or label is conducted.

The flow path has an internal thickness, e.g. internal diameter, so that cells can be detected in small amounts, preferably as single cells. Accordingly, the internal thickness is restricted. Preferably, the flow path has an internal thickness of 1 mm or less, preferably 550 µm or less, more preferably 100 µm or less or even 50 µm or less. Cells of interest should still be capable to pass the flow path. Thus, it has preferably an internal thickness of 5 µm or greater. The flow path is preferably a capillary.

In many cases, the electroporation of cells or a subgroup of cells (specific treatment) depends on the electric field strength of the applied electric field, which in the present invention lies between 50 V/cm and 50 kV/cm, preferably the applied electric field is from 100 V/cm to 30 kV/cm, from 500 V/cm to 20 kV/cm, or 1 kV/cm to 10 kV/cm, preferably from 2 kV/cm to 5 kV/cm. Especially preferred is a range of 5 kV/cm to 8 kV/cm or 25 kV/cm to 50 kV/cm (especially for lysis). The efficiency of the electric field is also influenced by the field profile, such as pulse shapes, like a periodic field or wave form of the applied electric field. The cell's sensitivity is also affected by the duration of the exposure time they are exposed to the electric field. In the inventive flow system, these exposure times are usually short, such as below 1 s. Of course, combinations of these electrical parameters, e.g. electric field strength, exposure time and frequency, can be used to treat cells more precisely. These disclosed ranges for the applied electric field may also represent ranges for the electric field in the sample, especially cells in the sample. Reversible electroporation may be used to transfer compounds into cells, e.g. transfection. The flow channel portion with the electrodes is a flow-through chamber. It has at least one inlet and one outlet for the sample. Thus, the chamber can be referred to as channel. Of course, several chambers or channels can be provided. If the chamber is a channel, electroporation and/or lysis can be performed while the sample is flowing through the channel. As already mentioned, the biological sample can be a blood sample, a saliva sample, a urine sample or any other sample that contains cells. During electroporation and/or lysis, compounds can be added to the biological sample. For example, a subgroup can be loaded with markers, stainings or DNA while another subgroup remains unloaded.

Also relevant, and proportional to the electric field strength, is the ratio of the potential difference between the electrodes and the distance between the electrodes. This ratio is preferably in the range of 500 V/cm to 50 kV/cm, especially preferred between 50 V/cm and 50 kV/cm, preferably the applied electric field is from 100 V/cm to 30 kV/cm, from 500 V/cm to 20 kV/cm, or 1 kV/cm to 10 kV/cm, preferably from 2 kV/cm to 5 kV/cm. Especially preferred is a range of 5 kV/cm to 8 kV/cm or 25 kV/cm to 50 kV/cm (especially for lysis). This ratio is easier to determine than the field strength—any may be a preferred parameter to characterize the invention.

According to the invention, the electric field is generated by at least two electrodes which are coated with electrically non-conductive dielectric material. The coating at least covers the surface of the electrodes that faces the interior of the chamber. By consequence, it protects the conductive part of the electrode that is behind the coating from contact with the sample. The dielectric material is solid. The dielectric coating is considered to be part of the electrodes. Thus, the electrodes comprise an electrically conductive part, preferably a metallic part, and a dielectric coating. Thus, the distances between the electrodes actually refers to the distance between the coatings. The electrodes define a chamber in the flow path, in which the treatment with the electric field occurs. The electrodes are placed at the walls of the chamber/flow path or periphery of the chamber/flow path. The electrodes can be a part of or form an inner surface of the chamber/flow path, which inner surface is in contact with the biological sample. The electrodes can be essentially flat, flush with the rest of the inner surface or form a structure of any kind. In another embodiment, the electrodes protrude from the chamber's inner surface or form a recess of the chamber's inner surface so as to provide a homogenous electric field between the electrodes. Preferably, the electrodes are sheets that are parallel to each other. This will improve homogeneity of the electric field. In still another embodiment, the electrodes are located outside the chamber. However, it is important that the generated electric field penetrates the chamber and hence the sample. Thus at least two electrodes are supplied with different electric potentials. Preferably, the electrodes are disposed essentially opposite to each other. In a preferred embodiment, the electrodes are essentially flat and form two opposite inner surfaces of the chamber. In order to avoid or minimize an electrical current between the electrodes and other disadvantageous chemical reactions, the electrodes are coated with the dielectric material, such that only the dielectric material is in contact with the sample. Electrical current flow would lead to unfavourable side effects, such as (Joule) heating of the sample, electrolyse, pH changes or electrochemical processes which might negatively influence the sample. These side effects would interfere with the actual electroporation and/or lysis process and thereby aggravate specific electroporation and/or lysis. In order to reduce an unwanted potential drop in the coatings, the dielectric material has a relative permittivity greater than 3.9, preferably greater than 9, more preferably 60 or more. In literature, such a dielectric material is referred to high-k materials. Even higher relative permittivity is favourable, preferably 80 and higher. In particular preferred embodiments, the permittivity is from 3.9 to 20000, preferably 8 to 10000, in particular preferred 10 to 5000, or 50 to 1000, or even 40 to 500. As dielectric material any suitable dielectric material can be used, e.g. Titanium dioxide $TiO_2$, Silicon dioxide $SiO_2$, Barium titanate, strontium titanate, aluminium oxide or Niobium pentoxide, etc. Preferably, a dielectric material with semiconductive properties is used, so as to form a Schottky-diode between the metallic part of the electrode and the dielectric material. Titanium dioxide $TiO_2$ is an example for such a material. As the electrodes are coated with the dielectric material, the dielectrical material can be a thin layer on the electrodes. The material for the electrodes can be copper, gold, silver, platinum, titanium, aluminium, carbon or any other conducting material.

For the purpose of further reducing unfavourable side effects in connection with the electrodes, it is advantageous, if the dielectric material has a thickness below 1 μm, preferably in the range of 50 nm to 850 nm, more preferably in the range of 100 nm to 750 nm or in the range of 150 nm to 500 nm, especially preferred 200 nm to 400 nm. Also larger ranges are possible, e.g. 600 nm to 2000 nm or 700 nm to 1000 nm or 750 nm to 800 nm. Due to the small thickness of the dielectric material, which is coated on the electrodes, the potential drop along the dielectric material is kept low. Thus, the use of high electrical potential differences, which entail negative side effects, is avoided. Furthermore, the whole assembly can be realized as micro fluidic structure.

Preferably the electrodes are flat sheets or metallic material (with a passivation layer as described above). The surface facing the chamber that is able to be in contact with the sample in the chamber is preferably 50 $\mu m^2$ to 10000 $\mu m^2$, especially preferred 75 $\mu m^2$ to 7500 $\mu m^2$, 100 $\mu m^2$ to 3000 $\mu m^2$, even more preferred 500 $\mu m^2$ to 2000 $\mu m^2$. According to all embodiments of the invention, preferably the chamber has not more than two electrodes for treatment of the sample. In other embodiments, that are even more preferred, an array of electrodes is used for the treatment of the cells, which creates an array of electric fields by said electrodes. Several serially placed at least two electrodes (e.g. electrode pairs) constitute the array. Between each electrode pair (at least two electrodes at a segment (chamber) of the flow path) is a spacer with no electrode, which may be very small and only to prevent contact between the serially placed electrodes. The function of the array is to continuously treat a cell of interest (as detected in the detection apparatus) by subsequent electrodes, dependent on the flow speed through the flow path. This means that a cell of interest is treated in electric fields of all these electrodes (or electrode pairs) of the array. The electrodes may be switched off when the cell of interest has passed. Alternatively, the electrodes are always on and only switched off when a cell that should not be treated passes through the flow path segment at the electrodes. Preferably, the array consists of 1, 2, 3, 4, 5, 6, 7, 8, 9, 10 or more at least two electrodes (preferably electrode pairs) that create an electric field at their segment of the flow path. All preferred embodiments regarding sizes, dimensions, coating, passivation and electric field parameters apply to all electrodes individually. Preferably, the electrodes have the same size (in a flow path with a constant cross section). The chamber is preferably rectangular with the electrodes provided in parallel arrangement therein, forming the rectangular space. The electrodes in this size are preferably adapted for smaller voltages, such as 1 V to 45 V or preferably 5 V to 40 V.

In order to generate a high electric field strength of the electric field with a relatively small potential difference between the electrodes, the distance between the electrodes can be below 1 mm, preferably below 550 μm, more preferably below 100 μm or even below 50 μm, but greater than 5 μm. Preferably the distance between the electrodes is at 5 μm to 1 mm, preferably 10 μm to 800 μm, or 20 μm to 700 μm, or 30 μm to 600 μm or 40 μm to 550 μm, or 50 μm to 90 μm or 60 to 85 μm. Further preferred distances between the electrodes are 120 μm to 2 mm, 150 μm to 1750 μm, 250 μm to 1500 μm, 550 μm to 1200 μm, 600 μm to 1 mm or any combination of these ranges. This facilitates the implementation of the inventive method in a handheld device since small potential differences can be easily achieved by means of batteries. Additionally, due to the small distances between the electrodes, homogeneity of the electric field is enhanced.

In one embodiment of the invention, the potential difference between the electrodes is in the range of 1 V to 100 V, preferably in the range of 5 V to 80 V or even 7 V to 70 V, more preferably in the range of 10 V to 55 V, 11.8 V to 45 V, 12 V to 40 V, or even 15 V to 35 V. These potential differences can be easily generated by batteries preferably in combination with a voltage transducer, e.g. a DC/DC converter.

Preferably, the electric field is a periodic field with a frequency in the range of 0.1 Hz to 10 kHz, preferably in the range of 10 Hz to 1 kHz or even 20 Hz to 1 kHz, especially 50 Hz to 900 Hz, or 100 Hz to 800 Hz, or 150 Hz to 700 Hz or 200 Hz to 600 Hz, wherein the wave form of the electric field is preferably a square wave, a sinusoidal wave or at least one pulse. Frequencies around 100 HZ, such as 80 Hz to 200 Hz are especially preferred. In further preferred embodiments, high frequency fields are used, such as an electric field with a periodic field with a frequency in the range of 0.1 kHz to 10 MHz, preferably in the range of 10 kHz to 1 MHz or even 20 kHz to 1 MHz, especially 50 kHz to 900 kHz, or 100 kHz to 800 kHz, or 150 kHz to 700 kHz or 200 kHz to 600 kHz, wherein the wave form of the electric field is preferably a square wave, a sinusoidal wave or at least one pulse. The periodic field can be unipolar or bipolar. Further, the field can be alternating periodically. The pulses are preferably unipolar, with a determined on-time and a determined off-time. In one embodiment, the pulses are rectangular. In another embodiment, the pulses are exponential decay pulses, wherein the rising edge has a step form, i.e. a vertical slope with a very short rise time, and the falling edge is exponentially falling, i.e. has a fall time longer than the rise time, such as multiple times longer, e.g. 5 times, 10 times, 20 times, 100 times or more or any range between these values. By means of exponential decay pulses, unwanted current pulses due to capacitive discharging in the sample can be avoided with the falling edge. The wave form can also have a positive or negative offset. The wave form can also be cut off partially. Any other methods for shaping the wave form can be used, such as pulse-width modulation. The above explanations are applicable for the potential difference between the electrodes and the electric field strength, as the potential difference is related to the electric field strength.

In a preferred embodiment, the number of pulses is kept in the range from 1 to 40000 or 10 to 30000, preferably in the range from 50 to 20000, more preferably in the range from 100 to 10000 or 150 to 8000, in particular preferably in the range from 200 to 8000 or 400 to 7000. Other favourable ranges, particularly for delivering compounds into cells, are 1 to 100 pulses, 1 to 70 pulses, 1 to 40 pulses, 1 to 15 pulses or 1 to 7 pulses. Other favourable ranges are 1000 to 20000 pulses, 1000 to 15000 pulses, 1000 to 10000 pulses, 1000 to 5000 pulses or 1000 to 3000 pulses. The frequency at which the above mentioned number of pulses are applied is preferably in the range of 10 Hz to 5 MHz, preferably, 100 Hz to 2 MHz, more preferably 800 Hz to 1.5 MHz, or any of the above mentioned frequencies, including the "high frequency fields". "Pulse" refers to one monopolar excitation to a maximum (such as at the indicated potential/voltages discussed above) that drops towards to baseline excitation, such as one-half sinusoid period or one square pulse, or one exponentially falling pulse.

In preferred embodiments, the exposure time of the biological sample lies in the range of 0.1 second to 20 seconds, preferably in the range of 0.2 seconds to 12 seconds, more preferably 0.3 to 7 seconds or 0.8 to 6 seconds. Exposure time should be selected according to the flow speed of the sample through the electrodes (and the detector). At a given flow speed, exposure time may be modified by selecting a corresponding length and number (array, see above) of the electrodes/chamber in the direction of flow. Such a length may e.g. be 1 cm to 50 cm, such as 2 cm to 40 cm, 3 cm to 30 cm or 4 cm to 20 cm or any range in between these values.

Example values for the volume of the chamber between the electrodes are in the range of 0.001 to 30 ml, preferably 0.01 to 25 ml, or 0.1 ml to 20 ml, 0.2 ml to 15 ml, 0.5 ml to 12 ml, 1 ml to 10 ml or 1 ml to 5 ml.

For further processing the biological sample, the sample can optionally be filtered for concentrating the cells after lysis and/or electroporation. For instance, the flow path can lead to a filter to concentrate and purify particles or cells un-affected from electroporation and/or lysis. The collected and optionally purified or filtered cells can be cultured for maintenance or propagation.

Electroporation can be used to collect material from or introduce material into the cell. Such material can be compounds of the cell, such as RNA or proteins. Material introduced into the cells is usually nucleotides, especially RNA or DNA or small molecule compounds of a size of up to 1 kDa. Preferably markers, labels or dyes are introduced into the cell, such as radiolabels or fluorescent labels.

Through experiments it has been shown that a reduced electrical conductivity in the sample leads to a reduction of the required field strength for electroporation and/or lysis when using the inventive chamber. Therefore, it is favourable if prior to exposing the biological sample to the electric field, an electrical conductivity reduction of the sample below 1 mS/cm, preferably in the range of 10 µS/cm to 800 µS/cm or 60 µS/cm to 560 µS/cm, by means of ionic exchange, transversal diffusion, filtering, dilution, buffer exchange or electrophoretic separation is conducted. The conductivity reduction can be conducted in a separate or in the same device as the inventive method. In experiments, it could be shown that by means of conductivity reduction, the rate of electroporation and/or lysis could be enhanced. In the prior art, usually $MgCl_2$ is added to the sample for electroporation. According to the invention, it is preferred to add alkali metal ions, especially Li+ or Na+ or $PO_4^{3-}$ ions, lysis and/or electroporation rate could be improved. Preferably the alkali metal ions are with a halogen counterion, such as Cl$^-$. Preferably, the concentration of the added molecules or salts lies in the range of 0.001 mM to 100 mM, preferably 0.01 mM to 50 mM, more preferably in the range of 0.05 mM to 10 mM for Li, Na, such as LiCl, NaCl, $MgCl_2$, $H_xPO_4$ or combinations thereof. "mM" refers to the unit millimolar. In case of combinations, these indicated concentrations refer to a sum concentration of these (alkali) metals combined.

In preferred embodiments of the invention, a further pair of electrodes, forming another chamber in the flow path, this time upstream of the detector (flow cytometry) is located. This further pair of electrodes can be used to treat the cells by electroporation without lysis, such as to load the cells with a marker or label as described above. Otherwise, the upstream electrodes work and are shaped the same as the above described downstream electrodes, which are preferably used for lysis or expelling cellular contents, like proteins, DNA, RNA, organelles, etc. as described above, with or without lysis.

Thus, prior to flow cytometry, the biological sample can be exposed to the electric field in the inventive chamber for electroporation and loaded with markers, stainings or other compounds.

In a preferred embodiment, two inventive chambers with electrodes are used, wherein the chambers are in fluid connection with the flow cytometry unit. One of the chambers is arranged upstream to the cytometry device and the other chamber is arranged downstream to the cytometry device. This arrangement can be accommodated in a single device or separated from each other. In this preferred embodiment, the sample is loaded with markers, stainings or other compounds in the first chamber, then transferred to the flow cytometry unit via fluid connection. After analysis or identification of cells in the flow cytometry unit, the sample is transferred to the second chamber via fluid connection. On the basis of the analysis or identification of the flow cytometry unit, the identified subgroups can be electroporated or lysed in the second chamber.

The invention may further comprise a unit that activates the electric field between the electrodes (downstream of the detector) when a detected cell passes between said electrodes in dependence of the flow speed. Such a control unit may calculate the time needed for cell to reach the electrodes after detection and time-dependently activate the electrodes. The control unit may also activate upstream electrodes as described above, usually for loading of cells trough electroporation.

The present invention is further illustrated by the following figures and examples, without being limited to these embodiments of the invention.

EXAMPLES

Production of Titanium-Oxide Coated Electrodes

Figure 1:
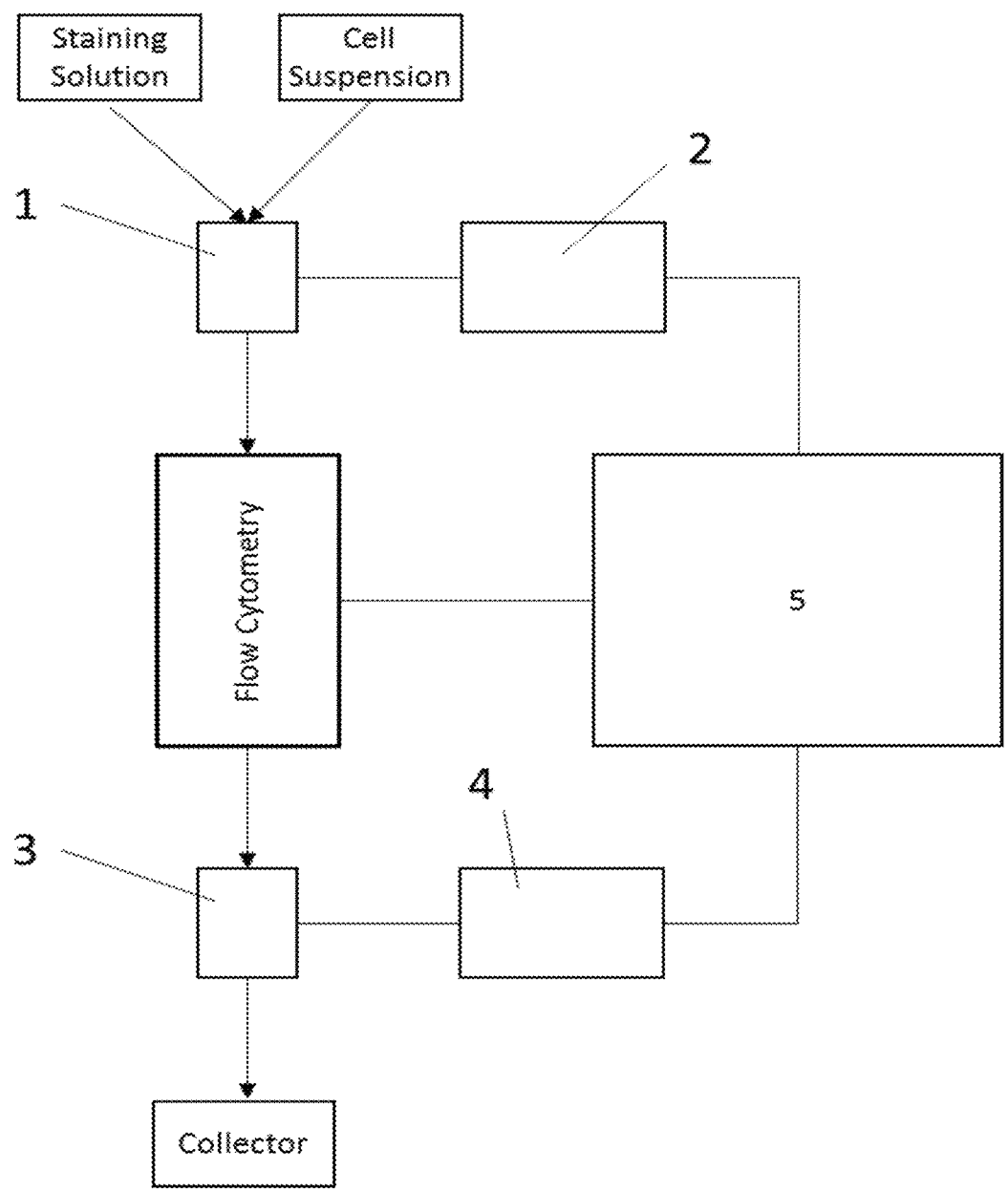
FIG. 1 shows a flow cytometry application in connection with the inventive method and device for specific electroporation and/or lysis. The flow cytometry system includes a device (1) upstream of the FC analysis to enable loading of cells and particles with stainings, markers or other cargo through the application of capacitive coupled electric fields, a device (3) downstream of the FC analysis to enable targeted permeabilization or lysis of cells or particles via capacitive coupled electric fields. Each device (1 and 3) is connected to the FC control system (5) via electronic control units (2 & 4) for a defined activation of the capacitive coupled electric fields.

Grade 2 titanium foil (commercially pure titanium, cpTi, 99.2% pure) was cut in dimensions of 60×10 mm. These electrodes were cleaned and coated using a previously established protocol (Wassermann et al. 2016). This treatment yields an average oxide layer thickness of 500-600 nm. Electroporation reservoirs were assembled using double-sided 81.3 µm thick adhesive tape (Adhesive Research, Arcare 90445) spaced 2.5 mm apart forming a 12,15 µl channel.

Cell Culture

Human embryonic kidney cells 293T (supplied by the Department of Nanobiotechnology of the University of Natural Resources and Life Sciences, Vienna) were cultivated at 37° C. and 5% $CO_2$ in DMEM (Thermo Fisher, 41965) supplemented with 10% FBS (Thermo Fisher, 10500) and 1% Pen/Strep Antibiotic—Antimycotic (Thermo Fisher, 15240). Cells were passaged by washing with PBS (1× from stock: Thermo Fisher, 70011044) followed by trypsinization (0.25%, Thermo Fisher, 25200) for 5 min at 37° C. Any sterile protocols were processed in biological safety cabinets. (Herasafe KS, Class II, Thermo Fisher, 51022488)

Sample Preparation

Cells were washed with PBS, detached by trypsinization and re-suspended in supplemented DMEM Medium. Electroporation buffer (EPB) was prepared from autoclaved 250 mM sucrose solution. PBS was added to adjust the desired sample conductivities. Conductivity was measured using a conductivity meter (B-771 LAQUAtwin, HORIBA Advanced Techno). Cells were centrifuged for 5 min at 400 g (RT), supernatant discarded and re-suspended with EPB. After two washing steps, cells were counted and adjusted to 1×10^6/ml with the next reconstitution. Final conductivity was recorded. If the suspension deviated more than 10 µS/cm from the calibrated EPB, the washing step is repeated until conductivity is within this range. Cell death from sample preparation was also assessed. Only samples containing more than 90% live cells, as determined by Hoechst 33342 stain were used for experiments.

Transfection

Cells were kept in a sterile working environment. 9 µl were placed on hydrophobic parafilm and mixed with 1 µl vector stock solution for a final working concentration of 25 ng/ml pTurboRFP-N (Evrogen, FP232) and 0.5 mM MgCl2. The suspension was aspirated into the electroporation chamber (FIG. 1, Ref. 1) and exposed to 10 exponential decay pulses of 40V at 1 kHz followed by 1000 exponential decay transfer pulses of 15 V at 50 Hz. They were ejected into an 8-well p-slide (Ibidi, 80826) and left to rest for 5 minutes. 250 µl OptiMEM (Thermo Fischer, 31985062) was added with gentle re-suspension. Transfected cells were cultivated at 37° C. and 5% CO2 for 48 hours and imaged by a digital camera (Prosilica GT, Allied Vision) mounted on an inverted microscope (CKX41 Fluo V2, Olympus). The fraction of cells expressing RFP was assessed from manual count of bright-field and red fluorescence overlays of at least 5 images from random positions in each respective well.

Electroporation and Imaging 293T cell lysis is used as an indirect readout to analyze the biological impact of capacitively coupled electric fields across a range of parameters. Cells in EP buffer were transferred to hydrophobic parafilm in 10 µl droplets and aspirated with the electroporation tip prototype. Electric fields were induced by applying the according voltage waveforms by a function generator (DG4102, Rigol) connected to a voltage amplifier (Falco WMA-300, Falco Systems, Netherlands). Voltages and current (via a 2Ω resistor) were monitored by an oscilloscope (DS1104B, Rigol). Cells were ejected onto parafilm and mixed with a 10 µg/ml (10×) stock solution of in PBS for a final concentration of 1 µg/ml. The sample was transferred to a hemocytometer (Thoma, Optik Labor) and imaged by a digital camera (Prosilica GT, Allied Vision) mounted on an inverted microscope (CKX41 Fluo V2, Olympus). Bright-field images were recorded for total cell count. To identify lysed cells, Hoechst 33342 viability dye was excited at 360 nm using a UV light source (X-Cite 120Q, Excelitas Technologies) and emission above 420 nm imaged for further analysis. For permeabilization experiments, the cell suspension is mixed 1:10 with a 30 µg/µl solution of Propidium Iodide (PI) prior to field exposure. The dye is prepared from dilution of a 1 mg/ml stock with electroporation buffer to limit any conductivity change. To identify permeabilized cells, the membrane impermeable PI was excited from 480-550 nm using a UV light source (X-Cite 120Q, Excelitas Technologies) and emission above 590 nm imaged for further analysis.

Data Analysis

Lysis images were analysed in Fiji (Schindelin et al. 2012) by adjusting the threshold to include positive cells only, isolating high-contrast live cells in bright-field and stained dead cells in fluorescence images. After converting images to binary, cell count was performed by particle analysis function. Results are displayed as percentage lysed, excluding the fraction of dead cells from sample preparation, which means that the control is always displayed as zero percent lysis. PI-positive cells were counted manually from a bright-field and red fluorescence overlay. Controls were overexposed to the point where PI-negative cells remain invisible. This setting is then applied to samples subjected to electric fields. Dead cells show high-PI fluorescence, look visibly dead in bright-field and are calculated equally as in lysis experiments. Permeabilized cells are displayed as the fraction of visibly live cells with any PI fluorescence.

Device Assembly and Use

As shown in FIG. 1, the present invention includes an apparatus for loading cells or particles with molecules within a fluid flowing through a microfluidic device (1) and using capacitive coupled electric fields. The apparatus includes an electric control system (2) connected to the FC control system (5) that outputs an electrical signal to the microfluidic device bearing electrodes covered with a high-k passivation layer that couple an electric field into the fluid flowing through the microfluidic device. The electric fields permeabilize the cells or particles to allow external molecules to enter the cells or particles before they are sent to the flow cytometer.

Targeted permeabilization of single cells or particles within a fluid flowing through a microfluidic device (3) occurs after passing through the flow cytometer analysis region. The apparatus includes an electric control system (4) connected to the flow cytometer control system (5) that outputs an electrical signal to the microfluidic device (3)

bearing electrodes covered with a high-k passivation layer that couple an electric field into the fluid flowing through the microfluidic device. The electric fields permeabilize the cells or particles after they passed through the FC analysis to allow either the targeted irreversible electroporation of single cells via negative or positive selection based on the FC analysis or to allow the targeted reversible electroporation of cells via negative or positive selection based on the FC analysis.

Lysis and Electroporation Settings

Figure 2:
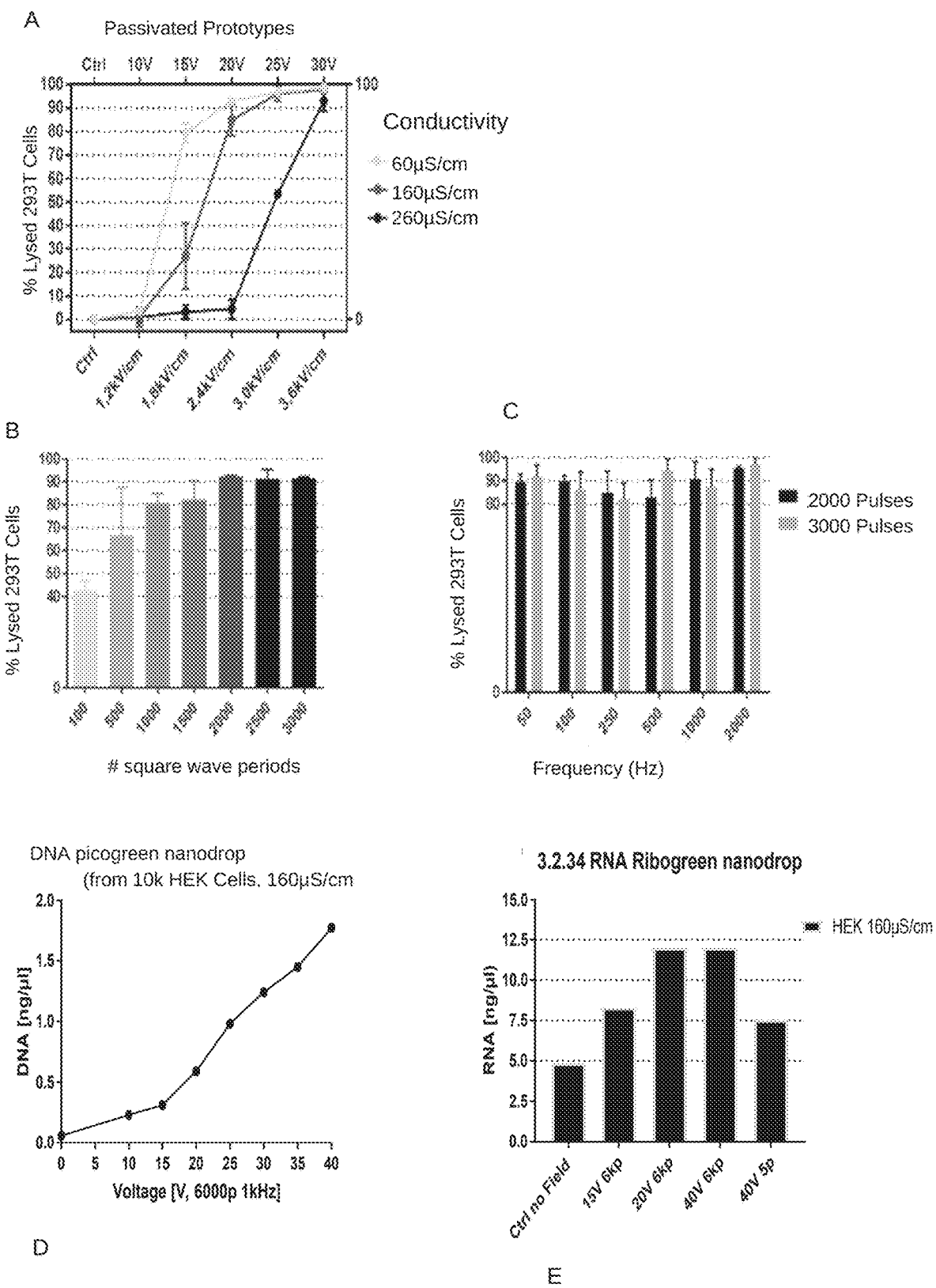
FIG. 2. Image A shows the lysis efficiencies for 293T cells using coated electrodes and buffers with different conductivities (60, 160 and 260 µS/cm). Cells were exposed to 6 seconds of AC square wave pulses at a frequency of 1 kHz (n=3). Image b shows the lysis efficiency of different pulse numbers at 1 kHz. Image C shows the frequency dependency at equal pulse numbers. In the images A to D the wave form refers to full square waves. Conductivities range between 160-170 µS/cm. n=3. Image D refers to measurement of cell-free DNA after lysis of HEK cells. Image E refers to the measurement of cell-free RNA after lysis of HEK cells.

The experiments described are intended to demonstrate controllable low voltage cell lysis in the electrode chamber microfluidic device. FIG. 2A shows lysis curves of 293T cells for different conductivities when applying capacitive coupled electric fields with a square wave 1 kHz AC signal for 6 seconds. For a conductivity of 60 µS/cm, lysis begins at 10 V and reaches a plateau at 25 V. Increasing conductivity to 160 µS/cm, we observe lysis starting below 15 V and peaking at 25 V. With 260 µS/cm, onset of lysis occurs at 20 V and reaches its maximum around 30 V. The dynamic range for all three conductivities spans 10 V, corresponding to 1.2 kV/cm. It was shown that lysis efficiency of 293T cells is inversely proportional to buffer conductivity. This trend is highly reproducible and lysis curves are clearly distinguished by minor changes in buffer composition.

FIG. 2B shows experiments with pulse number as the only variable. Field strength was set to 3.6 kV/cm and frequency at 1 kHz. As a result, lysis efficiency increases steadily with period number up to 2000 periods, reaching a plateau of maximum efficiency with around 90% lysis and minimal standard deviation for a given conductivity.

FIG. 2C shows 293T cell lysis upon exposure to 2000 pulses at different frequencies. While the total exposure time if significantly different, adjustment to the previously determined threshold of 2000 pulses results in equal lysis efficiency independent of frequency.

FIG. 2D shows the concentration of cell-free DNA after lysis of 293T cells with increasing applied voltages.

FIG. 2E shows the concentration of cell-free RNA after lysis of 293T cells with increasing applied voltages.

Figure 3:
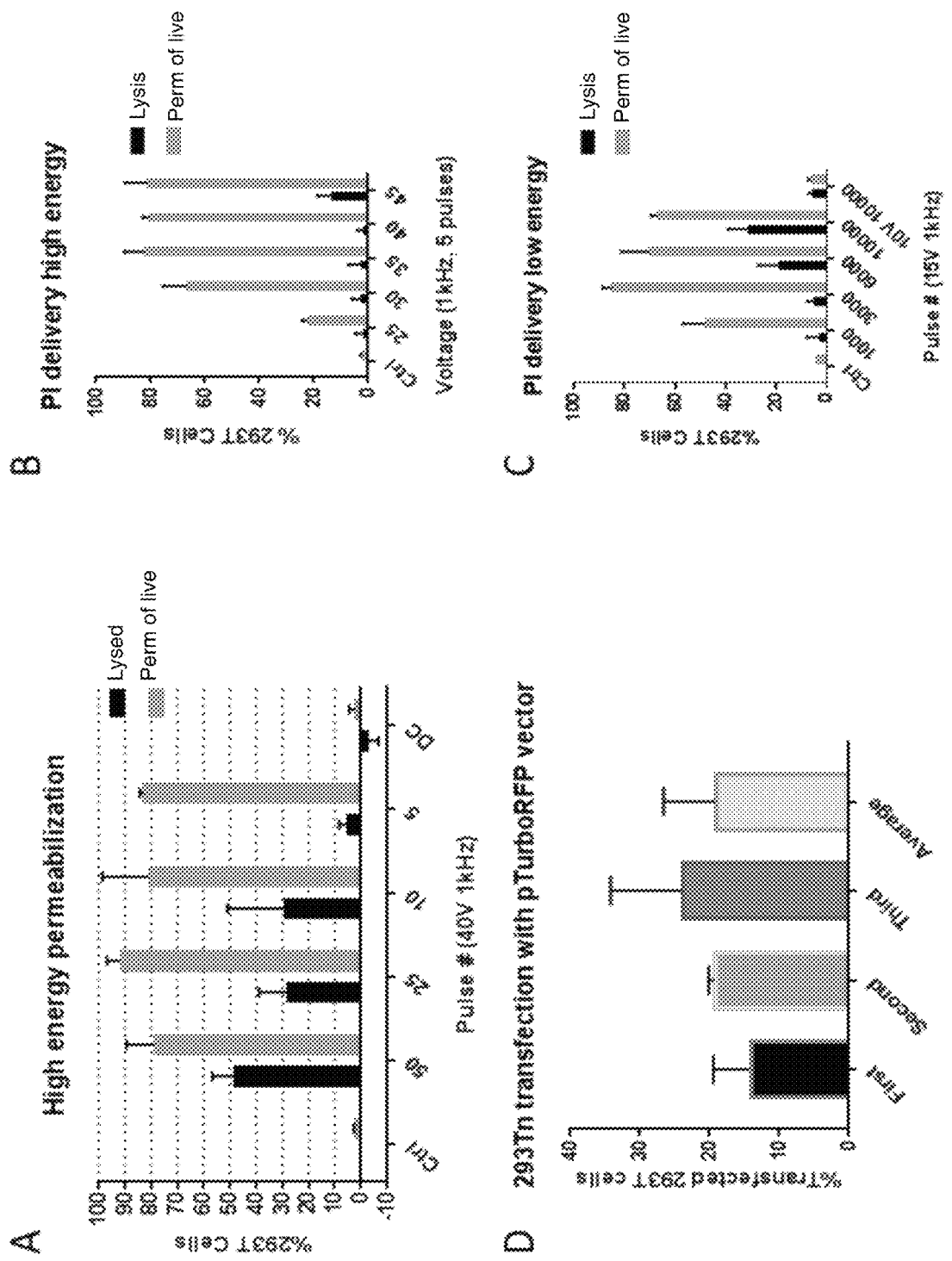
FIG. 3. 293T cell lysis and permeabilization after exposure to an electric field. Image A shows 293T cell lysis and permeabilization after exposure to decreasing pulse number of 40 V square waves, Image B shows 5 square wave pulses of increasing voltage. Image C shows an increasing number of 15V square wave pulses. (D) Technical replicates of 293T transfection with pTurboRFP plasmid upon exposure to 10 exponential decay pulses of 40V at 50 Hz and 1000 exponential decay transfer pulses of 15 V at 50 Hz. Bars show percentage of cells expressing RFP 48 hours after treatment as detected by fluorescence microscopy.

For uptake demonstration, FIG. 3A shows lysis and propidium iodide (PI) delivery into 293T cells when exposed to a decreasing number of high-voltage square wave pulses. 50 pulses of 40 V lead to lysis of 48.5% of cells while PI was taken up by 78.8% of the remaining viable cells. Decreasing the number of pulses further results in higher viability while the fraction of live cells permeable to PI remains similar. Upon exposure to 5 square wave pulses of 40 V, 5.6% of 293T cells are lysed by the electric field while 82.8% are viable and PI-positive.

FIG. 3B shows further optimization of PI-delivery by changing the applied voltage. Cells were subjected to 5 square wave pulses at 1 kHz repetition rate. Viability is virtually unaltered by the field magnitude in this pulse range. 293T cell viability is decreased by 2.5% by application of five 25 V pulses while five 40 V pulses decrease viability by 1.8%.

FIG. 3B further shows a correlation between field strength and the fraction of PI-permeable cells, yielding 22.4%, 66.7%, 82.3%, 80.5% and 81.1% for 25 V, 30 V, 35 V, 40 V and 45 V respectively.

FIG. 3C shows that PI-permeabilization strongly correlates with pulse number at the same voltage. 1000 square wave pulses yield 48.4% PI-positive viable 293T cells, increasing up to 85.0% at 3000 pulses with minimal loss of viability.

FIG. 3D shows 293T cells expressing RFP 48 hours after electro-transfection with pTurboRFP-N plasmid by application of exponential decay pulses of 40 V to the pipette tip.

The invention claimed is:

1. A method for lysis or electroporation of cells in a biological sample comprising the following steps:
    passing cells of the sample, through a flow path with a flow speed, wherein the flow path runs through a detection apparatus for detecting individual cells and wherein the flow path comprises an array of two or more segments of the flow path, each said segment of the array comprising at least two electrodes for generating an electric field, and which electrodes are located downstream of the detection apparatus and which electrodes are coated with a dielectric material with a relative permittivity greater than 3.9, wherein the coating at least covers the surface of the electrodes that faces the flow path; and
    when the presence of a specific cell is detected in the detection apparatus, then generating an electric field between the electrodes when the detected cell passes between the electrodes in dependence of the flow speed, wherein the array of segments generates an array of electric fields, wherein the electric fields cause electroporation or lysis of the cell.

2. The method according to claim 1, wherein the strength of the electric field is in the range of 500 V/cm to 50 kV/cm.

3. The method of claim 2, wherein the strength of the electric field is in the range of 1 kV/cm to 20 kV/cm.

4. The method of claim 2, wherein the strength of the electric field is in the range of 1 kV/cm to 10 kV/cm.

5. The method according to claim 1, wherein the potential difference between the electrodes for generating the electric field is in the range of 1 V to 100 V.

6. The method of claim 5, wherein the potential difference between the electrodes for generating the electric field is in the range of 5 V to 80 V.

7. The method of claim 5, wherein the potential difference between the electrodes for generating the electric field is in the range of 7 V to 70 V.

8. The method of claim 5, wherein the potential difference between the electrodes for generating the electric field is in the range of 10 V to 45 V.

9. The method of claim 5, wherein the potential difference between the electrodes for generating the electric field is in the range of 10 V to 30 V.

10. The method according to claim 1, wherein the biological sample comprises cells of a first group and cells of a second group, wherein cells of the first group are exposed to a first electric field with a first electric field strength and cells of the second group are exposed to a second electric field with a second electric field strength.

11. The method according to claim 10, wherein the first electric field causes lysis of the cells of the first group and the second electric field causes reversible electroporation of the cells of the second group.

12. The method according to claim 1, wherein the biological sample comprises cells of a first group and a second group, wherein cells of the first group are exposed to a first electric field with a first electric field strength that causes lysis or reversible electroporation of the cells of the first group and wherein the electric field is deactivated for cells of the second group.

13. The method according to claim 1, wherein the dielectric material has a thickness below 1 µm.

14. The method of claim 13, wherein the dielectric material has a thickness in the range of 50 nm to 650 nm.

15. The method of claim 13, wherein the dielectric material has a thickness in the range of 100 nm to 500 nm.

16. The method according to claim 1, wherein the distance between the electrodes is below 1 mm.

17. The method of claim 16, wherein the distance between the electrodes is below 550 µm.

18. The method of claim 16, wherein the distance between the electrodes is below 250 µm.

19. The method of claim 16, wherein the distance between the electrodes is below 100 µm but greater than 5 µm.

20. The method according to claim 1, wherein the electric field is a periodic field with a frequency in the range of 0.1 Hz to 10 MHz, wherein the wave form of the electric field is a square wave, a sinusoidal wave or at least one pulse per period.

21. The method of claim 20, wherein the electric field is a periodic field with a frequency in the range of 10 Hz to 1 MHz.

22. The method of claim 20, wherein the electric field is a periodic field with a frequency in the range of 50 Hz to 500 KHz.

23. The method according to claim 1, wherein specific cells are collected after flowing through a chamber with the at least two electrodes.

24. The method according to claim 1, wherein prior to passing the cells through the detection apparatus, electroporation for loading the cells with a marker is conducted.

25. The method of claim 1, wherein passing the cells of the sample through the flow path comprises passing the cells of the sample suspended in a fluid through the flow path.

26. The method of claim 1, wherein the relative permittivity is greater than 9.

27. The method of claim 1, wherein the relative permittivity is greater than 60.

28. The method of claim 1, wherein between the segments in the flow path is a spacer without an electrode.

29. The method of claim 1, wherein the array of segments of the flow path comprises three or more segments.

30. The method of claim 1, wherein the flow path comprises at least two further electrodes upstream to the detection apparatus, and which further electrodes are coated with a dielectric material with a relative permittivity greater than 3.9, wherein the coating at least covers the surface of the electrodes that faces the flow path, wherein prior to passing the cells through the detection apparatus, the cells are electroporated by the further electrodes for loading the cells with a marker or label.

31. The method according to claim 30, wherein the marker or label is selected from the group consisting of a radioactive label, a fluorescent label and a dye.

* * * * *